(12) United States Patent
Mo

(10) Patent No.: US 6,594,527 B2
(45) Date of Patent: Jul. 15, 2003

(54) ELECTRICAL STIMULATION APPARATUS AND METHOD

(75) Inventor: Y. Joseph Mo, Princeton, NJ (US)

(73) Assignee: NexMed Holdings, Inc., Robbinsville, NJ (US)

( * ) Notice: Subject to any disclaimer, the term of this patent is extended or adjusted under 35 U.S.C. 154(b) by 0 days.

(21) Appl. No.: 09/824,362

(22) Filed: Apr. 2, 2001

(65) Prior Publication Data

US 2001/0034544 A1 Oct. 25, 2001

Related U.S. Application Data

(63) Continuation-in-part of application No. 09/156,968, filed on Sep. 18, 1998, now abandoned.

(51) Int. Cl.$^7$ ................................................. A61N 1/18
(52) U.S. Cl. ............................................................ 607/74
(58) Field of Search ................................ 607/59, 70–74, 607/39, 46

(56) References Cited

U.S. PATENT DOCUMENTS

| | | | |
|---|---|---|---|
| 4,913,148 A | 4/1990 | Diethelm | 128/421 |
| 4,919,139 A | 4/1990 | Brodard | 128/421 |
| 4,922,906 A | 5/1990 | Takeuchi et al. | 128/419 R |
| 5,107,835 A | 4/1992 | Thomas | 128/419 R |
| 5,117,826 A | 6/1992 | Bartelt et al. | 128/421 |
| 5,133,351 A | 7/1992 | Masaki | 128/419 R |
| 5,133,352 A | 7/1992 | Lathrop et al. | 128/419 R |
| 5,607,461 A | 3/1997 | Lathrop | 607/75 |
| 6,083,250 A | 7/2000 | Lathrop | 607/50 |

Primary Examiner—Scott M. Getzow
(74) Attorney, Agent, or Firm—Olson & Hierl, Ltd.

(57) ABSTRACT

An electrical stimulation apparatus and method for providing electrical stimulation to tissue. The electrical stimulation apparatus includes a base unit and an electrode module. The base unit is configured to be hand portable and contains a first electrical circuit and a first battery for supplying electrical energy to the first electrical circuit. A second electrical circuit and a second battery provide a time/date function. The base unit supports an LCD to provide a visual indication of the various functions of the electrical stimulation apparatus. The electrode module is programmable to enable the prescribing physician to set the treatment protocol for the electrical stimulation apparatus. The present apparatus is particularly well suited for the treatment of herpes simplex and herpes zoster.

6 Claims, 4 Drawing Sheets

ELECTRICAL STIMULATION APPARATUS AND METHOD

CROSS-REFERENCE TO RELATED APPLICATION

This application is a continuation-in-part of co-pending U.S. Ser. No. 09/156,968, filed on Sep. 18, 1998 now abandoned.

FIELD OF THE INVENTION

This invention relates to the electrical stimulation of tissue for the treatment of selected physiological conditions and, more particularly, to a novel electrical stimulation apparatus and method having an interchangeable electrode module, the electrode module serving as an activation key and being preprogrammable to deliver a predetermined treatment protocol for the particular physiological condition.

BACKGROUND OF THE INVENTION

Various skin lesions such as those resulting from acne and herpes virus are known to be amenable to treatment through the use of electrical stimulation. Although various theories have been advanced to explain this phenomena, to date, no satisfactory explanation has been put forth as a rationale for why these types of skin conditions can be successfully treated using electrical stimulation. In spite of this lack of explanation, various devices have been developed for the delivery of electrical stimulation to tissue. For example, U.S. Pat. No. 5,117,826 teaches a device for the combined nerve fiber treatment and body stimulation while U.S. Pat. No. 5,133,352 teaches a method for treating herpes simplex. A small size, low frequency curing apparatus is shown in U.S. Pat. No. 4,922,906. An electrotherapeutic treatment apparatus is shown in U.S. Pat. No. 5,107,835. U.S. Pat. No. 4,913,148 discloses the treatment of herpes simplex I and II as well as herpes zoster. A low frequency electrotherapeutic device is disclosed in U.S. Pat. No. 5,133,351.

Each of these devices apparently resulted from the search for a device that could be used for the various therapeutic purposes as disclosed in the description of the device and its intended use. It is clear from the foregoing that electrical stimulation can be beneficial if appropriately applied to the area requiring treatment. Appropriate application includes, for example, predetermining the correct voltage of the electrical stimulation, the pulse waveform, if any, the amperage, and the application duration, to name several. Clearly, each application requires that each of the foregoing elements of the electrical stimulation must be tailored to meet the specific requirements for each patient.

In view of the foregoing, it would be an advancement in the art to provide an electrical stimulation apparatus and method wherein the apparatus is preprogrammable to provide each patient with the appropriate electrical stimulation as a function of the patient condition to be treated. It would also be an advancement in the art to provide the electrical stimulation apparatus with a replaceable electrode module. It would be an even further advancement in the art to provide the electrode module with a logic circuit to allow the electrode module to be preprogrammed with the predetermined operating parameters for the electrical stimulation apparatus. It would be an even further advancement in the art to provide an electrical stimulation apparatus that provides both the patient and the treating physician with the capability of monitoring treatment progress with the electrical stimulation apparatus. Such a novel invention is disclosed and claimed herein.

SUMMARY OF THE INVENTION

A novel electrical stimulation apparatus having a hand-held housing and a replaceable electrode module is provided as well as a method of treatment. The housing includes a first electrical circuit and a first battery for the operation of the electrical stimulation function by alternating monopolar bursts of current. A second electrical circuit and second battery provides a time/date function. A key in the electrode module enables energization of the aforementioned first electrical circuit. A liquid crystal display (LCD) on the housing is coupled to both the first and second electrical circuits and provides a visual display of the various functions of the electrical stimulation apparatus including a treatment timer, an ON/OFF indicator, a battery status indicator, an indicator for the number of remaining treatments available, a screen prompt, a treatment indicator, treatment cycle indicator, an audio indicator (beeper), visual bars, and a time/date display, respectively. The electrode module is provided with a programmable probe control logic to allow the electrical stimulation apparatus to be selectively programmed for each particular application.

The present apparatus and method are particularly well suited for the treatment of herpes simplex and herpes zoster. For this purpose, the apparatus is programmed to apply seriatim a pair of alternating monopolar bursts of current to a skin region to be treated. The monopolar bursts of current can have a current intensity of up to about 30 milliamperes and a duration of about 10 seconds each. Preferably a time interval of about one second at no current flow (i.e., a current intensity of zero) is maintained between the monopolar bursts of alternating polarity.

In general, the prescribing physician prescribes the appropriate treatment protocol which is entered into the programmable probe control logic of the electrode module. The patient obtains the preprogrammed electrode module under prescription and plugs it into the hand-held housing where the preprogrammed prescription is relayed to the first electrical circuit in the housing. The operating instructions to commence the treatment protocol are visibly displayed on the LCD to instruct the patient in the operation of the stimulation apparatus. Importantly, the electrode module is specifically programmed to meet the treatment requirements of the individual patient during the treatment process and, equally importantly, the electrode module is programmed to cease functioning upon completion of its programmed treatment cycle. This latter feature is designed to encourage the patient to return to the prescribing physician for further analysis of the patient's condition and thereby enable the physician to selectively alter the treatment protocol as programmed into the electrode module in order to more suitably treat the patient.

DETAILED DESCRIPTION OF PREFERRED EMBODIMENTS

Figure 1:
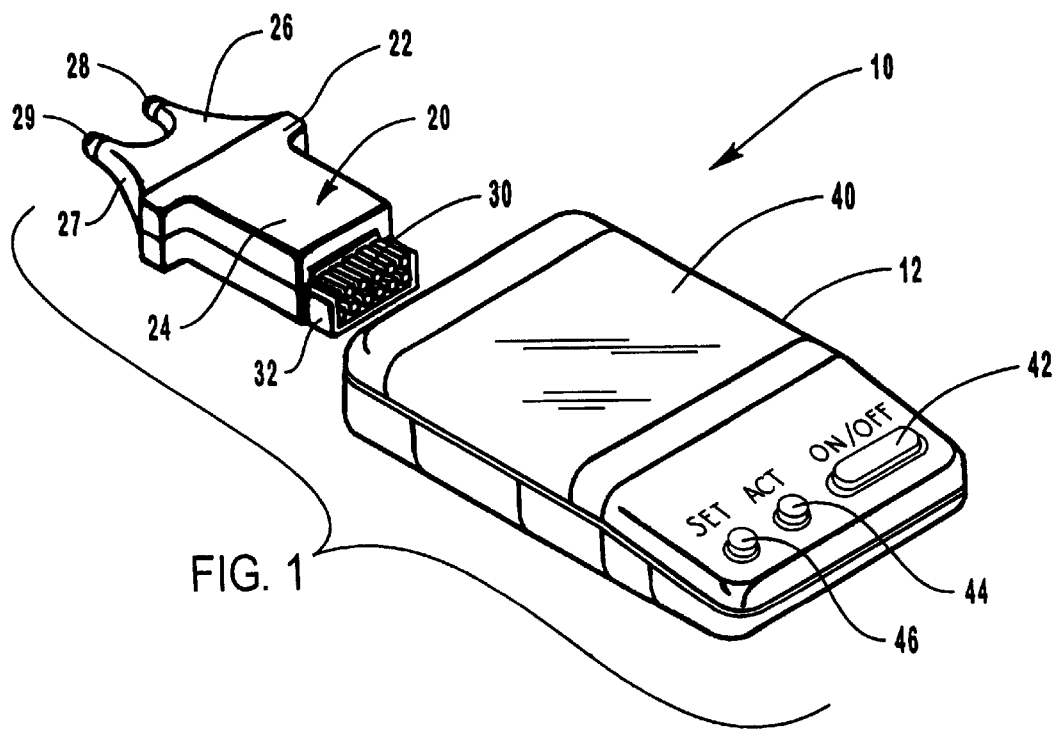
FIG. 1 is an exploded, perspective view of the electrical stimulation apparatus of this invention showing the electrode module prior to engagement with the housing.

The invention is best understood from the following description with reference to the drawings wherein like parts are designated by like numerals throughout and taken in conjunction with the appended claims.

General Discussion

My novel electrical stimulation apparatus and method in one aspect is designed to provide the prescribing physician with the capability of selecting a specific treatment protocol for the particular condition to be treated using electrical stimulation. In another aspect, a predetermined fixed treatment protocol is provided. The electrical stimulation apparatus can be provided as a single unit or it can be provided as a two-component device, a base unit and an electrode module which includes a key. This latter configuration is the preferred configuration for several reasons. The electrode module can be made disposable not only for sanitary reasons but also to require the patient to refill the prescription with another electrode module in the event further treatment is required. This procedure not only allows the physician to more closely monitor the patient's use of the electrical stimulation apparatus, but it also allows the physician to change the prescription as the treatment progresses.

The electrode module is provided with a logic circuit that allows the electrode module to be preprogrammed with the instructions for the specific treatment parameters. These parameters include a current dosage amount (milliamperes and microvolts), current profile (whether steady state or pulsatile), waveform, and the number of treatments and the duration of the treatments. Once the prescribed number of treatments has been delivered by the logic circuit, the electrode module is programmed to cease operating, thereby requiring the patient to obtain a replacement electrode module which is available only by prescription. By adopting this procedure the physician is able to more closely monitor the treatment of the patient as well as reduce instances of the electrical stimulation apparatus being shared among patients, thus reducing cross contamination between patients by infected electrodes. The programmability of the electrode module also allows the physician to selectively prescribe different treatment parameters for the electrical stimulation apparatus as the treatment progresses whether treating acne, herpes lesions, carpal tunnel syndrome, psoriasis, or the like.

The base unit contains a first battery which provides power to administer the dose of electrical current for the treatment function. A second battery provides electrical energy to a circuit that controls all functions related to the LCD screen, clock, and timer. The LCD screen is capable of displaying a plurality of messages such as a clock/alarm, an ON/OFF notice, an "INSERT KEY" notice for enabling energization of the first circuit, a battery level indicator, an alphanumeric remaining dosage indicator, a current power Hi/M/Lo meter, a "PUSH ACT TO START" notice, a flashing circle to indicate dosage delivery, a dosage bar, and a time/date display.

Operationally, pressing the ON/OFF switch to turn on the electrical stimulation apparatus results in the system being activated. In the event the electrode module has not been electrically coupled to the base unit, the LCD screen will flash the message "INSERT KEY." Once the key (electrode module) has been inserted into the base unit, the first circuit can be energized, and one of the messages Hi, M, or Lo is displayed indicating, respectively, high, medium, or low, to indicate the level of dosage set by the preprogrammed logic circuit in the electrode module. Simultaneously, the alphanumeric indicator will also display the number of remaining treatments, again, as set by the preprogrammed electrode module. A battery symbol will also be displayed to provide a visual indication of the battery status. This battery status is for the battery that provides current for a dose. If the battery charge is too low, a dose cannot be dispensed. A "PUSH ACT TO START" display flashes to indicate to the patient that the ACT button should be pushed to energize the first circuit. Once the ACT button has been pushed, a small circle flashes at a rate of one flash per second to indicate that the electrical stimulation treatment is being delivered to the electrodes. Simultaneously, the alphanumeric display changes from the number of treatments available to display the word "go" to indicate that the electrical stimulation apparatus is in operation. During treatment, the dosage bar is created as a horizontal array of vertical bars with each vertical bar being created in one second increments until the treatment has concluded and the dosage bar is filled. Also, a short beep tone is generated at a predetermined rate, usually one to four beeps per second during the treatment.

Completion of the treatment cycle causes the alphanumeric indicator to display the letters "OK," the circle to stop flashing, the dosage bar to be filled, and a long beep tone of one second duration. After a brief delay, the LCD screen resets to its beginning display.

Detailed Description

Figure 2:
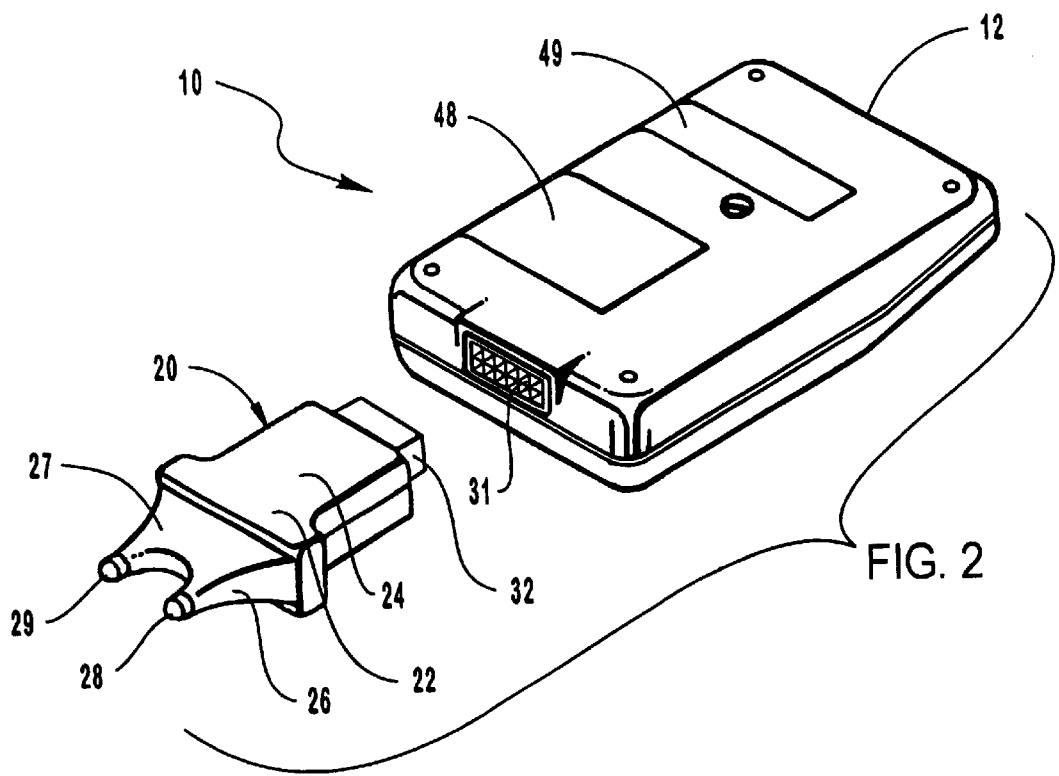
FIG. 2 is a perspective view of the back side of the electrical stimulation apparatus of FIG. 1.

Referring now to FIGS. 1 and 2, the novel electrical stimulation apparatus of this invention is shown generally at 10 and includes a housing 12 and an electrode module 20 provided with a key that enables energization of the first circuit. Housing 12 is configured to be hand portable and has an external dimension comparable to a small pocket calculator thereby rendering electrical stimulation apparatus 10 readily transportable and accessible for immediate use whenever the requirement arises. Housing 12 includes an LCD screen 40, an ON/OFF switch 42, an ACT switch 44, and a set switch 46, the function of each of which will be discussed more fully hereinafter. Housing 12 also includes battery covers 48 and 49 (FIG. 2), each of which is removable to provide access to the respective batteries, battery 58 and clock battery 66 (FIG. 3) housed within housing 12.

Electrode module 20 includes a body 22 having a base 24 at one end and extending into a generally twin pyramidal configuration formed with a first apex 26 and a second apex 27. First apex 26 serves as a support for a first electrode 28 while second apex 27 serves as a support for a second electrode 29. First electrode 28 and second electrode 29 are a fixed distance apart, with the result that the applied voltage differential between first electrode 28 and second electrode 29 is approximately constant (and thus the delivered current intensity for a given pair of monopolar bursts of current) when electrical stimulation apparatus 10 is being used properly and first electrode 28 and second electrode 29 are in contact with the user's tissue to be stimulated. A first connector 30 constituted by a plurality of prongs extends outwardly from base 24 and serves as an electrical connector for electrically coupling electrode module 20 to housing 12 by engaging a second connector 31 (FIG. 2) in the end of housing 12. A partial enclosure 32 shields a plurality of prongs that constitute first connector 30 against damage and together with connector 30 also provides a reliable key for keying electrode module 20 to housing 12 in the correct orientation. Preferably, partial enclosure 32 is configured vis-a-vis second connector 31 so that insertion can be effected only in one position, i.e., when the prongs of first connector 30 are electrically matingly aligned with receptacles therefor in the second connector 31. For example, partial enclosure 32 and the space around second connector 31 can be asymmetric so that coupling can be achieved in only one position. Alternately, second connector 31 can be fixed in housing 12 so that the U-shaped partial enclosure 32 can be received in housing 12 only on that side of second connector 31 which provides electrically mating alignment of the prongs in first connector 30 with the corresponding receptacles in second connector 31.

Figure 3:
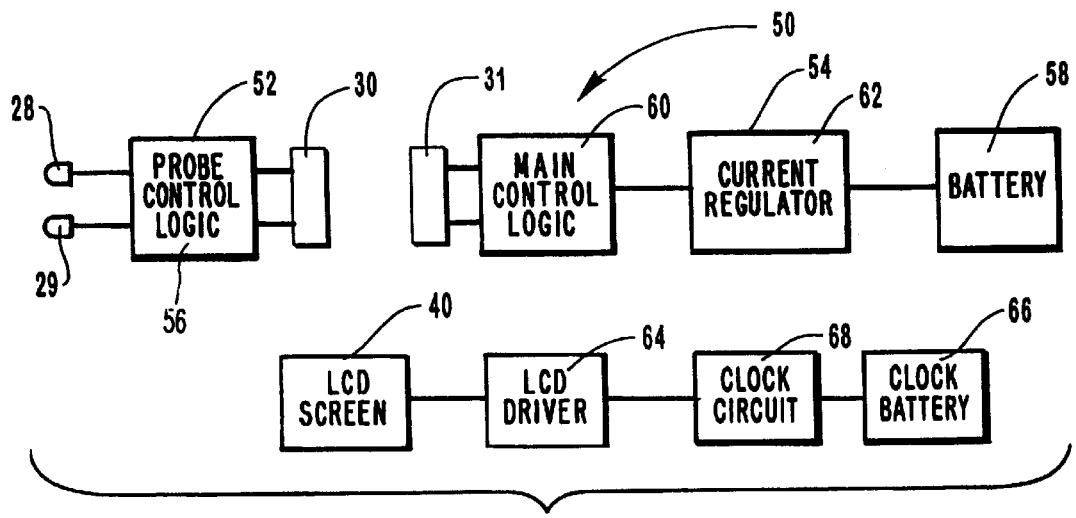
FIG. 3 is a schematic diagram of the circuitry of the electrical stimulation apparatus of FIGS. 1 and 2.

Referring now to FIG. 3, a schematic of the electronic circuitry of electrical stimulation apparatus 10 (FIGS. 1 and 2) is shown generally as circuit 50 and includes an electrode module circuit 52 and a base circuit 54. Electrode module circuit 52 is housed within electrode module 20 (FIGS. 1 and 2) and is electrically coupled to base circuit 54, housed within housing 12, by electrical contact being made between first connector 30 and second connector 31. Electrode module circuit 52 consists of a probe control logic 56 which is electrically coupled to electrodes 28 and 29. Probe control logic 56 is preprogrammable in order to provide the necessary instructions for the operation of base circuit 54. In particular, probe control logic 56 is selectively preprogrammed with such features as the total number of treatments available with the particular electrode module 20 along with the type, duration, and electrical energy of the specific electrical stimulation. This feature provides the prescribing physician with the ability to closely monitor the treatment program of the particular patient. Control over the number of treatments available significantly reduces the likelihood of cross contamination between patients caused by sharing electrical stimulation apparatus 10 since only a limited number of treatments are available per each prescription as preprogrammed into electrode module 20. The limited number of available treatments also requires the patient to return to the prescribing physician on a regular basis to thereby provide the prescribing physician with the capability of more closely monitoring the treatment progress, and, advantageously, selectively altering the treatment protocol as contained in the memory of probe control logic 56.

Figure 9:
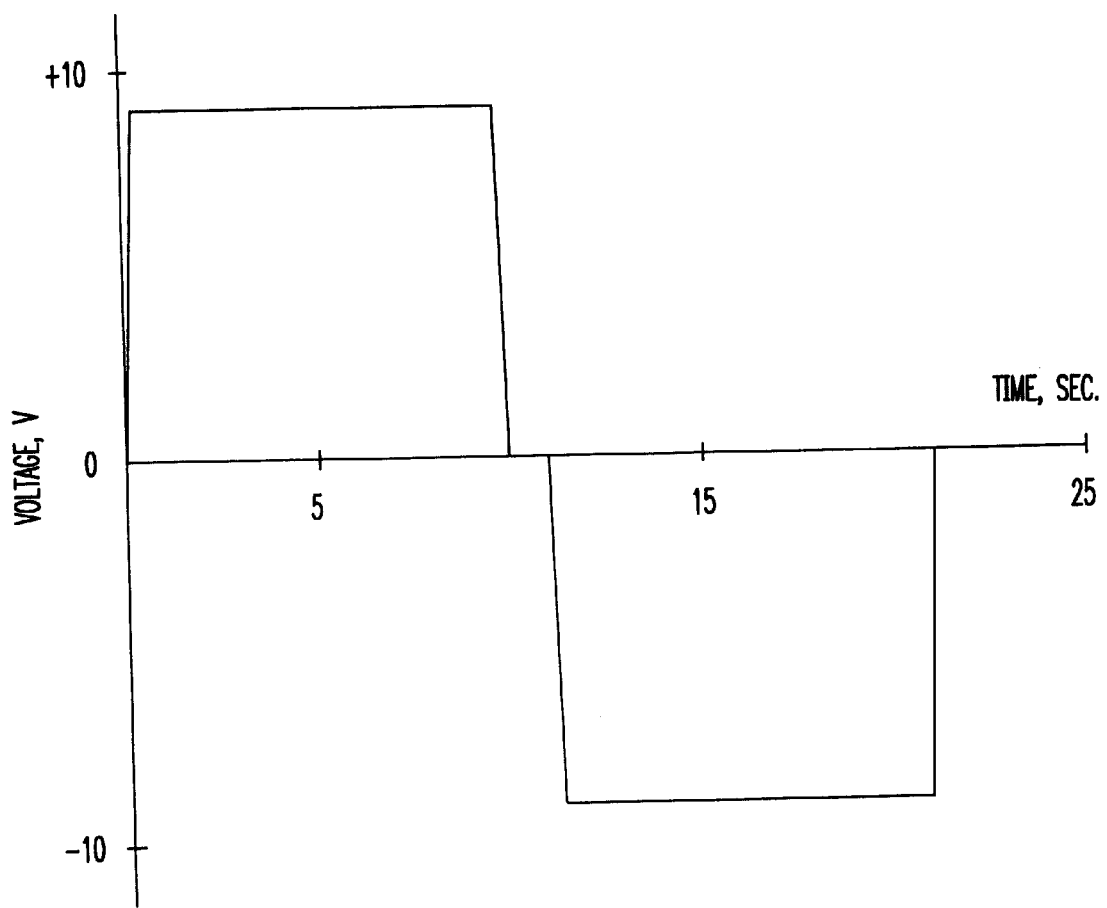
FIG. 9 is a graphical representation of the preferred output of an electrical stimulation apparatus embodying the present invention.

Desirable results have been achieved when paired extended stimulating monopolar current bursts of opposite polarity are provided to the patient's tissue situated between electrodes 28 and 29. In a preferred embodiment, each stimulating burst of current lasts no more than about ten seconds. The voltage differential across electrodes 28 and 29 preferably is about 9 volts, and the current intensity can be up to about 30 milliamperes. Preferred such current intensities for each burst are 9 milliamperes, 18 milliamperes, and 27 milliamperes. Desirable results have further been achieved when there is a period of no more than about 2 seconds between the first extended stimulating burst and the second extended stimulating burst of opposite polarity from that of the first stimulating burst of electrical energy. Thus, in a particularly preferred embodiment, the pair of stimulating bursts comprise a first burst of about 27 milliamperes with a 9 volt differential between electrodes 28 and 29 lasting about 10 seconds, followed by a one second period during which no electrical stimulation is provided and thereafter followed by a second burst of about 27 milliamperes with a 9 volt differential between electrodes 28 and 29 lasting about 10 seconds, with the first burst and the second burst having opposite polarity (FIG. 9).

Base circuit 54 includes a battery 58, a main control logic 60 and a current regulator 62. Current regulator 62 and main control logic 60 provide the predetermined electrical stimulus to electrodes 28 and 29 as preset in the memory of probe control logic 56. A second battery, battery 66, drives an LCD driver 64 and a clock circuit 68 which provides a continuous time and date display on LCD screen 40. LCD driver 64 provides the necessary electronic processing to present the predetermined information displayed on LCD screen 40 as will be discussed more fully hereinafter.

Figure 4:
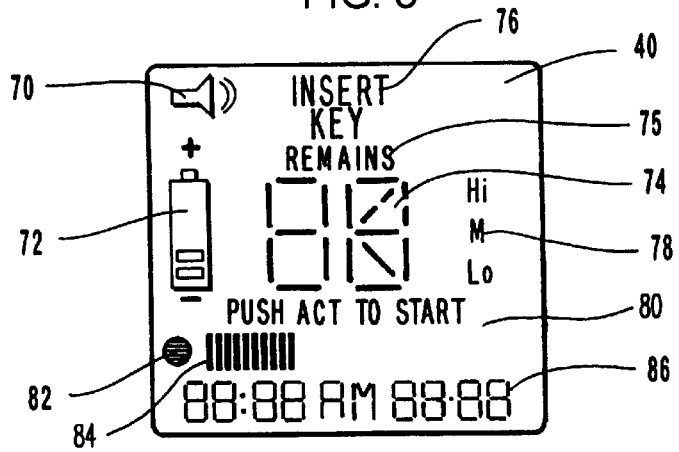
FIG. 4 is an enlargement of the LCD screen shown in FIG. 1 showing all of the display features of this novel electrical stimulation apparatus.

Referring now to FIG. 4, LCD screen 40 is shown with all of the displays possible thereon. These displays include a horn icon 70; a battery symbol 72; an alphanumeric display 74; an INSERT KEY prompt 76; a dosage power indicator 78 shown as one of "Hi," "M," or "Lo" to indicate high, medium, or low, respectively; a PUSH ACT TO START prompt 80; a circle 82; a dosage bar 84; and a time and date display 86. Each of these features will be discussed more fully hereinafter with respect to the description of the functions shown in FIGS. 5–8. Time and date display 86 is operational at all times regardless of the status of electrical stimulation apparatus 10 (FIGS. 1 and 2) and regardless whether electrode module 20 is mounted to housing 12.

Figure 5:
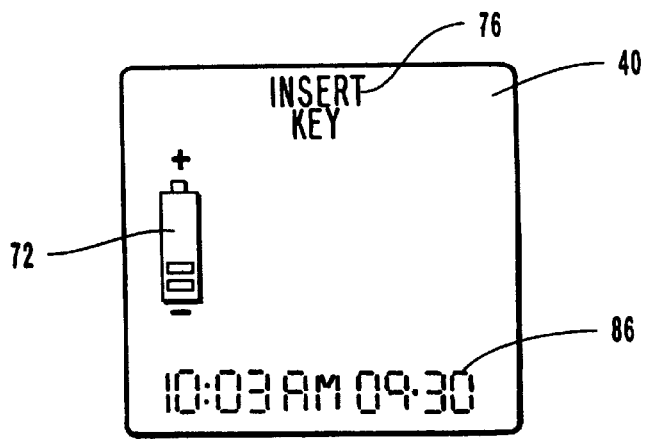
FIG. 5 is the display of the LCD screen of FIG. 4 prior to insertion of the electrode module.

Referring now to FIG. 5, LCD screen 40 is shown upon initial activation of ON/OFF switch 42 (FIG. 1). At this stage, battery symbol 72 is displayed along with INSERT KEY prompt 76 which instructs the user to electrically couple electrode module 20 to housing 12 by keying first connector 30 and partial enclosure 32 to housing 12 and second connector 31. This display on LCD screen 40 occurs only if electrode module 20 is electrically uncoupled from housing 12 and ON/OFF switch 42 has been activated to the ON position. LCD screen 40 always shows time and date display 86 regardless of the position of the ON/OFF switch 42.

Figure 6:
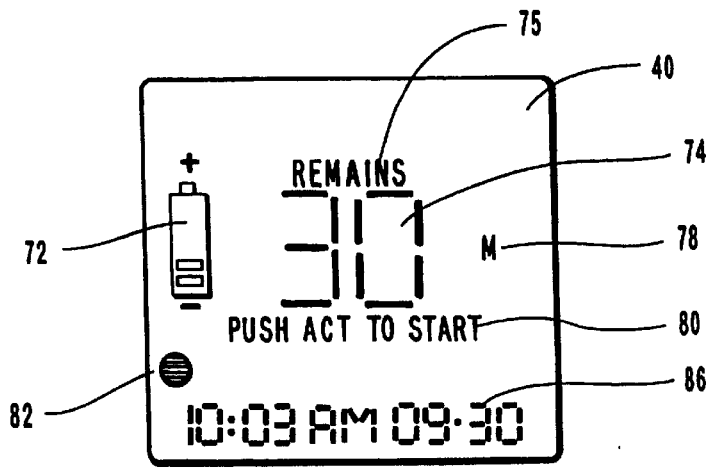
FIG. 6 is the display of the LCD screen prior to the start of the treatment protocol.

Referring now to FIG. 6, LCD screen 40 is shown at its display configuration when electrode module 20 is electrically coupled to housing 20 with ON/OFF switch 42 turned to the ON position and prior to initiation of the treatment process by electrical stimulation apparatus 10. In particular, battery symbol 72 is displayed to show the status of battery 58 while dosage power indicator 78 displays the symbol "M" to indicate medium dosage power as preprogrammed into probe control logic 56 (FIG. 3). Alphanumeric display 74 displays the numeral 30 indicating that thirty remaining dosages are available with electrical stimulation apparatus 10. This designation is indicated by the presence of REMAINS reminder 75. PUSH ACT TO START prompt 80 is displayed to alert the user to the next step in the treatment procedure and circle 82 is displayed as a solid display.

Figure 7:
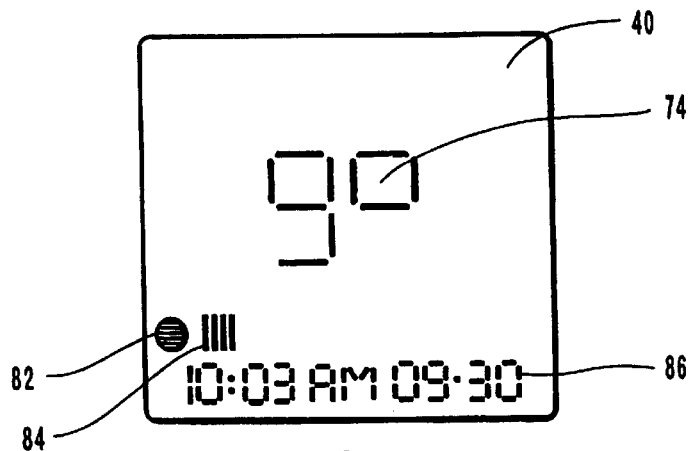
FIG. 7 is the display of the LCD screen during treatment showing the time remaining for the treatment cycle.

Referring now to FIG. 7, LCD screen 40 is shown immediately upon activation of ACT button 44 wherein circle 82 commences flashing or otherwise pulsing in a light and dark manner at one second intervals while alphanumeric display 74 reads "go." Simultaneously, dosage bar 84 commences to progressively fill with a plurality of vertical bars advancing from the left toward the right. Each vertical bar represents a one second period of time in the treatment protocol.

Figure 8:
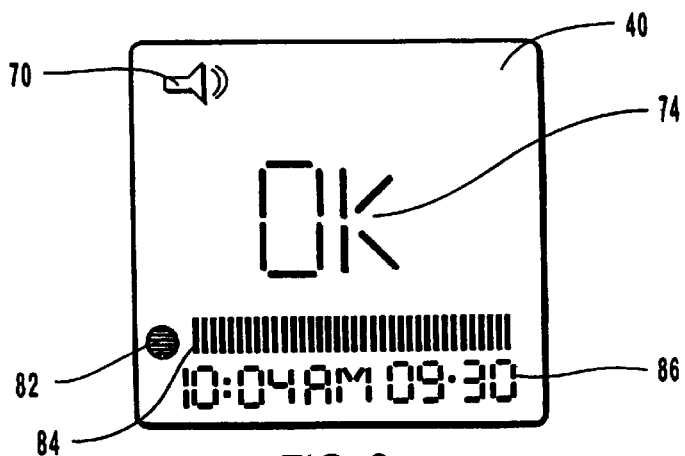
FIG. 8 is the display of the LCD screen upon completion of the treatment cycle.

Referring now to FIG. 8, LCD screen 40 is shown immediately upon completion of the treatment cycle in that alphanumeric display 74 now reads OK to indicate successful completion of that particular treatment cycle with electrical stimulation apparatus 10. Further, circle 82 is a steady, solidly colored circle and dosage bar 84 is completed with a plurality of vertical bars. This display is held for several seconds and an audible tone is emitted as visually indicated by the horn icon 70. After a preset period of time, LCD screen returns to a blank screen with the exception of time and date display 86.

FIG. 9 illustrates graphically the current intensity and polarity of current bursts delivered during a single treatment. As shown in FIG. 9, a single current burst of positive polarity is delivered first at a voltage of about 9 volts for about 10 seconds and is followed, after about a one second interval of no current, by a current burst of negative polarity at a voltage of about 9 volts for about 10 seconds. The delivered current intensity for each burst is about 27 milliamperes.

The Method

In the practice of the method of this invention using electrical stimulation apparatus 10, the prescribing physician provides to the patient a prescription to enable the patient to obtain electrical stimulation apparatus 10 wherein probe control logic 56 in electrode module 20 has preprogrammed therein all of the predetermined operational parameters for electrical stimulation apparatus 10 as prescribed by the physician. These parameters include, for example, the number of treatments prescribed, their duration and frequency, and the electrical characteristics of the electrical stimulation including the voltage, amperage, waveform, amplitude, and frequency, if any, to name several. Each of these parameters are predetermined by the prescribing physician in order to meet the particular requirements for treating the physiological condition diagnosed whether acne, herpes simplex, herpes zoster, carpal tunnel, eczema, psoriasis, dermatitis, or the like. Advantageously, probe control logic 56 is selectively programmable to provide electrode module 20 with the specific operational instructions to suitably control main control logic 60. Further, since electrode module 20 is preprogrammed for the treatment of a specific condition of a specific patient there is a significantly reduced likelihood that the patient will share electrical stimulation apparatus 10 with another patient thus significantly reducing cross contamination between patients.

After having obtained electrical stimulation apparatus 10 with electrode module 20 and having probe control logic 56 suitably programmed the patient activates ON/OFF switch 42 where the appropriate prompt is displayed on LCD screen 40. For example, in the event electrode module 20 is not electrically coupled to housing 12, or more particularly, to base circuit 54 the screen prompt on LCD screen 40 will display as prompt 76 the words "INSERT KEY" as shown in FIG. 5. The correct coupling of electrode module 20 to housing 12 changes LCD screen 40 to the display shown in FIG. 6. In particular, alphanumeric display 74 reads "30" which is an indication that thirty treatments remain in this particular configuration of electrode module 20 as shown by prompt 75 with the word "REMAINS." Prompt 80 instructs the patient to activate electrical stimulation apparatus 10 by pushing ACT switch 44. The patient places electrodes 28 and 29 in a bracketing position over the particular area to be treated and then pushes ACT switch 44. Alphanumeric display 74 changes from a display of the number of treatments remaining to the word "go" and dosage indicator 82 starts to flash while dosage bar 84 commences to fill sequentially with a plurality of vertical lines. Upon completion of the treatment cycle, dosage bar 84 is filled horizontally, dosage indicator 82 ceases to flash and becomes a solid circle, the word "OK" is displayed by alphanumeric display 74, and a tone is emitted as indicated by horn icon 70. The patient then returns electrical stimulation apparatus 10 to its storage position until time to initiate the next treatment sequence. If desired, electrode module 20 may be removed from housing 12 although this step is unnecessary in the event further treatments are available therein as determined by the programming of probe control logic 56.

Set switch 46 allows the patient to set the time and date display 86 by suitably controlling clock circuit 68 and/or to disable the audio indicator and its associated horn icon 70.

For treatment of herpes simplex and herpes zoster, the apparatus of the present invention is utilized to apply seriatim a pair of alternating monopolar bursts of current, substantially as illustrated in FIG. 9, to a skin region to be treated. The current intensity can be up to about 30 milliamperes for each burst of current. Each burst has a current duration of about 10 seconds, and consecutive bursts have opposite polarity. Preferred current intensities per burst are 9 milliamperes, 18 milliamperes, and 27 milliamperes. Also, preferably, a time interval of about one second at no current flow is maintained between consecutive bursts having opposite polarity.

The voltage to be applied across the electrodes of the apparatus in contact with the skin region to be treated will vary depending on the conductivity of the involved skin region. Usually, however, a voltage of about 9 volts is sufficient to provide the desired current intensity in the skin region to be treated.

Treatment frequency can vary from patient to patient. Preferably the pair of alternating monopolar bursts of current at the selected current intensity are applied daily to the skin region to be treated about every hour over an eight hour period, and over a time period of no more than five days. For treating herpes simplex, the treatment usually is carried out over a time period of one to three days. For treating herpes zoster, the treatment usually is carried out over a time period of one to four days.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrical stimulation apparatus comprising:

a housing;

a display on said housing for visually displaying selected information;

a first electrical circuit and a first battery electrically coupled thereto in said housing for electrical stimulation of tissue by a series of alternating monopolar bursts of current;

a second electrical circuit and a second battery electrically coupled to said second electrical circuit, said second electrical circuit providing a second source of electrical energy for operating said display;

an electrode module configured to be selectively coupled to said housing, in operable electrical connection with said first electrical circuit and including a key for enabling energization of said first electrical circuit.

2. The electrical stimulation apparatus defined in claim 1, wherein said key is associated with probe control logic for preprogramming said probe control logic with a preselected treatment protocol for said first electrical circuit.

3. The electrical stimulation apparatus defined in claim 2 wherein said key is configured as a disposable element to accommodate disposal of said key upon completion of said preselected treatment protocol.

4. The electrical stimulation apparatus defined in claim 2 wherein said display includes a prompt for prompting a user of said electrical stimulation apparatus to follow said preselected treatment protocol.

5. The electrical stimulation apparatus defined in claim 2 wherein said display includes a treatment status display for displaying the status of the treatment delivered by said electrical stimulation apparatus.

6. The electrical stimulation apparatus defined in claim 1 wherein said display includes a battery status display for displaying the status of said first battery.

* * * * *